United States Patent [19]
Goodbody et al.

[11] Patent Number: 4,831,133
[45] Date of Patent: May 16, 1989

[54] **EXTRACTION OF ALKALOIDS OF *CATHARANTHUS ROSEUS* TISSUE**

[75] Inventors: Anne E. Goodbody, Toronto; Colin D. Watson, North York; Masanaru Misawa, Weston, all of Canada

[73] Assignee: Allelix, Inc., Ontario, Canada

[21] Appl. No.: 45,621

[22] Filed: May 1, 1987

[51] Int. Cl.⁴ .......................................... C07D 519/04
[52] U.S. Cl. .................................................... 540/478
[58] Field of Search ......................................... 540/478

[56] References Cited

U.S. PATENT DOCUMENTS 4,172,077 10/1979 Jovanovics et al. ................. 540/478
4,749,787 6/1988 Guanasekera ...................... 540/478

FOREIGN PATENT DOCUMENTS 1094552 1/1981 Canada.

OTHER PUBLICATIONS

Scott et al., J. Am. Chem. Soc., vol. 100:19, pp. 6253-6255, (09/13/78).
Langlois et al., J. Am. Chem. Soc., vol. 98:22, pp. 7017-7024, (10/27/76).
Renaudin, Physiol. Veg., vol. 23(4), pp. 381-388, (1985).
Endo et al., Chemical Abstracts, vol. 108(11):93051d, (1987).
Endo et al., Chemical Abstracts, vol. 108(23):201668w, (1987).

*Primary Examiner*—Donald G. Daus
*Assistant Examiner*—Diana G. Rivers
*Attorney, Agent, or Firm*—Wyatt, Gerber, Burke & Badie

[57] ABSTRACT

Alkaloids present in *Catharanthus roseus* tissue are selectively concentrated by aqueous extraction of ground tissue followed by extraction with organic solvent e.g. ethyl acetate. The resultant concentrate is rich in catharanthine, vindoline and 3',4'-anhydrovinblastine (AVLB). Yield of AVLB is enhanced by addition to the aqueous extraction medium of acid, salt, or hydrogen peroxide and can be further enhanced through the addition of sodium borohydride.

18 Claims, No Drawings

EXTRACTION OF ALKALOIDS OF *CATHARANTHUS ROSEUS* TISSUE

FIELD OF THE INVENTION

This invention relates to alkaloids produced by the *Catharanthus roseus* plant.

BACKGROUND OF THE INVENTION

The low levels at which vinblastine and vincristine are produced naturally by *Catharanthus roseus* has prompted researchers to investigate the feasibility of using in vitro techniques to produce these pharmaceutically active compounds.

As a result of research in various areas, it is now generally understood that the monomeric alkaloids catharanthine and vindoline are the components which couple, in vivo, to form an intermediate compound 3',4'-anhydrovinblastine which is converted ultimately to form vinblastine. In turn, vincristine is generated from vinblastine. The overall reaction scheme can thus be represented as follows:

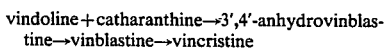

vindoline+catharanthine→3',4'-anhydrovinblastine→vinblastine→vincristine

To permit economical in vitro production of vinblastine and vincristine, efficient production of 3',4'-anhydrovinblastine (hereinafter referred to as AVLB) is necessary. The present invention is therefore concerned with a method of recovering AVLB for use particularly in the application of in vitro methods for producing the more valuable dimeric alkaloids vinblastine and vincristine.

REFERENCE TO THE PRIOR ART

Canadian Pat. No. 1,094,552 issued Jan. 27, 1981 describes a process for isolating vindoline, catharanthine and AVLB which comprises extracting dried leaves with organic solvent such as methanol or toluene or a mixture thereof and aqueous acid solution, purifying the extract using a phase-change method and then precipitating with sulphate addition. Thereafter, individual alkaloids or groups thereof are isolated from the mother liquor using chromatography, solvent gradients and/or pH differentials.

In *Physiol. Veg*, 1985, 23(4), 381-388 Renaudin describes an alkaloid extraction process in which suspension cells of *Catharanthus roseus* are extracted with 0.01% acetic acid, and collected in organic solvent fractions using a reverse phase cartridge after the pH of the acid extract is raised to pH 7.3-7.5 by NaOH addition. This particular extraction method is particularly suited to assay for alkaloid content using HPLC with fluorimetric detection.

Those familiar with alkaloid extraction techniques will appreciate that extraction processes vary depending on the chemical nature of the compound to be extracted. In this regard, AVLB demands special consideration given its propensity for oxidation to less important or less valuable alkaloids such as leurosine. Use of dried leaves in an extraction process as disclosed for example in the Canadian patent cited above is undesirable when AVLB is selected for recovery since the drying process is oxidative in nature and could reduce this available AVLB in the starting tissue.

In this same vein, pH elevation of an AVLB crude extract, as taught by Renaudin, such as by addition of sodium hydroxide may also contribute to AVLB oxidation and therefore reduce the AVLB available for recovery.

The oxidation of AVLB by prior art processes is reflected perhaps by the very modest yield of AVLB extracted by the process disclosed in the Canadian patent (0.145 grams from 1 kg dried leaves). Accordingly, it is an object of the present invention to provide a method suitable for extracting AVLB from *C. roseus* tissue.

SUMMARY OF THE INVENTION

As initial extraction agent, the present invention utilizes an aqueous medium of acidic pH. Use of aqueous, acidic medium rather than organic solvent in the initial extraction procedure offers several advantages. Primarily, the aqueous medium is selective in the sense that AVLB and other basic alkaloids are collected in the initial step rather than with a larger number of plant products in an organic solvent. In addition, cell debris including chloroplasts recovered in the aqueous medium can be removed by simple centrifugation thereby removing chlorophyll which otherwise could contribute to AVLB oxidation and may interfere with purification process. Removing chlorophyll from organic solvent requires a more complex technique.

After separating cell debris from soluble components such as by centrifugation, the soluble component is extracted with organic solvent. In accordance with a preferred embodiment, a reducing agent, preferably sodium borohydride, is added to the soluble component prior to organic solvent extraction. Addition of a reducing agent at this stage of the extraction procedure results in enhanced AVLB yield possibly by compensating oxidative agents or by converting oxidized AVLB derivatives to AVLB i.e. the iminium product of catharanthine and vindoline coupling is reduced by sodium borohydride to AVLB.

Once extracted with organic solvent, AVLB can be purified according to techniques standard in the art e.g. chromatographically, using selective crystallization etc.

In accordance with an embodiment of the invention preferred herein, the *C. roseus* tissue is digested with enzyme to disrupt cell walls and release alkaloids to the extent possible.

It should be noted that the present invention avoids the use of oxidative agents wherever possible. Accordingly, it is of the utmost preference herein to conduct the extraction process under inert atmosphere where possible, although significant AVLB yields can be obtained in normal atmosphere.

Thus, according to one aspect of the present invention there is provided a process for extracting AVLB from *C. roseus* tissue which comprises a first step in which the tissue is extracted in aqueous medium of acidic pH and a second step in which the soluble component is extracted with organic solvent.

DETAILED DESCRIPTION OF THE PREFERRED EMBODIMENTS

The extraction process may be conducted on fresh e.g. recently grown, or frozen *C. roseus* tissue. Tissue which has been dried is preferably avoided since the drying process is believed to have the effect of oxidizing AVLB in the tissue and therefore lowers the amount of AVLB available in dried tissue.

The fresh or frozen tissue is preferably minced prior to the first step in the extraction in order to expose cellular tissue. Fresh tissue may, for example, be homogenized in acid in a standard blender. Frozen tissue is suitably ground in liquid nitrogen. Since, however, it is always the intention herein to process the *C. roseus* tissue under non-oxidative conditions, it is most suitable to use grinding under inert atmosphere, to prepare the tissue for extraction, whether fresh or frozen tissue is selected as starting material.

It is believed that AVLB associates with the cell wall matrix possibly in the plant tissue or when cells are disrupted and contents mixed. It is possible therefore that while grinding of the tissue exposes a fractio of the AVLB to the initial extraction medium, a remaining fraction of the AVLB is still bound and will escape extraction. Accordingly, it is preferred herein to expose either the unground tissue or the ground tissue to enzymes capable of digesting the cell wall components, such as cellulase, pectinase, xylanase and laminarinase, before the extraction is carried out. Commercial preparations useful for this purpose are abundant and include, for example Macerozyme and Driselase (both products of Yakult Honsha Co. Ltd., Japan).

Once prepared, the tissue is first extracted with an aqueous medium having an acidic pH. Water per se may be used e.g. tap water, distilled or double distilled water, and may be preferred to keep costs at a minimum. However, experimentation reveals that lowering of the pH by adding acid to the aqueous medium can enhance AVLB extraction. For example AVLB yield when aqueous medium at around pH 2 is used has been found to be greater than the corresponding yield at around pH 6, all other conditions being equal. To lower the pH, any acid may be used, including organic acids such as acetic acid and inorganic acids such as sulfuric acid. Mineral acids such as hydrochloric acid are preferred and may be mixed with water to attain the desired pH prior to extracting the tissue therewith. The resulting pH of the aqueous medium may be within the range from 1.5 to 7.

The pH of the aqueous medium will become more basic after the *C. roseus* tissue is suspended therein. The pH elevation caused by tissue addition will vary, depending upon the amount and constitution of the tissue although a rise of from 1 to 2 pH units can be expected under typical conditions. However, provided that the initial pH of the aqueous medium is acidic, yield of AVLB is satisfactory. Preferably, the pH of the medium after tissue addition remains acidic, for example from pH 3.5 to pH 6.5, in order to obtain preferred yields. This can be accomplished by acidifying the aqueous medium, before tissue exposure, to generate an initial pH of about 1 or 2 pH units below the pH desired after tissue extraction. Alternatively, dilute acid may be added directly to the tissue extract, if necessary. What is important to bear in mind is that base addition to correct pH should be avoided since this will impact on the oxidation of AVLB and could lower yield.

While the effect of the acid in the extraction process is not completely understood, it is believed that the acid acts by dissociating AVLB from various macromolecules such as polysaccharides, proteins, polyphenols etc. A similar effect appears to occur when salt, rather than acid, is added initially to the aqueous medium in accordance with an alternative embodiment of the present invention. Although no acid is added, the salted aqueous medium is still considered herein to be an aqueous medium of acidic pH since addition of salt to water per se for example, still results in a medium having a pH of 7 or lower. The salts which are suitable for addition to the water include highly ionizable salts lsuch as ammonium sulphate, potassium chloride and especially sodium chloride. Salt concentration in the water can be in the range from 0.01–5.0M although, particularly in the case when sodium chloride is used, molar concentrations in the range from 0.9–3.0M are preferred. The salt can be added directly to water (about pH 6.0) and used as an extraction medium when the molar salt concentration is as desired.

In an additional embodiment of this invention, hydrogen peroxide is added to the acidic aqueous extract of *C. roseus* tissue to enhance the AVLB yields. Preferably, the amount of hydrogen peroxide added is above 8 mM, most preferably, it is 20 mM.

Once the ground and enzyme-digested tissue is suspended in the aqueous medium, whether water per se, acidified water or salted water is used, preferably with agitation, and optionally mixed with hydrogen peroxide, the soluble component containing the alkaloids is separated from cell debris i.e. the insoluble component for example by filtration or, more preferably, by centrifugation. Aqueous extraction of the insoluble component may be repeated to recover additional alkaloid in a soluble component which may then be pooled with previously collected soluble components.

Prior to extracting with organic solvent, it is in accordance with a preferred embodiment herein that a reducing agent is added to the soluble component. In this respect, sodium borohydride is particularly suitable in amounts sufficient, for example to establish a concentration in the soluble component in the range from about 0.05 mg/mL to about 4.0 mg/mL, more preferably in the range from 0.1 to 3.0 mg/mL. The reducing agent is believed to enhance AVLB extraction yield either by reducing an iminium analogue of AVLB or by hindering oxidation of AVLB in the soluble component. Best results are obtained after separation of soluble component from insoluble component. Addition of reducing agent prior to separation i.e. during extraction appears to reduce AVLB levels in the final extract.

The aqueous medium into which the alkaloids are initially extracted may be frozen, if desired, for at least as long as about three weeks before subsequent extraction with organic solvent.

Extraction of the soluble aqueous component with organic solvent, the second extraction step, is preferably conducted in a two phase system using, for example, an organic solvent selected from benzene, toluene and ethyl acetate of which the use of ethyl acetate is preferred. A series of organic extractions may be carried out on the same aqueous extract and the organic fractions pooled for further processing if desired.

Purification of the AVLB contained in the organic fraction may be carried out using techniques which are now standard in the art such as chromatography, crystallization etc. The extract which results from the extraction process described herein will be rich in the monomers catharanthine and vindoline. Detectable amounts of vinblstine are also present. Of particular relevance hereto is the presence, in the extract, of an enhanced proportion of AVLB which with extraction procedures preferred herein, can approach 0.2% by dry weight of tissue. This can be compared with the accepted values of about 0.0003% by dry weight for the alkaloids vinblastine and vincristine which can be prepared using AVLB as a precursor.

Thus, by providing a method for enhancing the extracted yield of AVLB, processes which utilize this precursor can become more economically attractive.

Embodiments of the invention are described hereinbelow by way of example only.

EXAMPLE 1

Broad Spectrum Analysis pH Effect

To a suspension medium consisting of 7.5 ml water (pH 5.9) and 1 gram NaCl was added 2.5 grams fresh weight of *C. roseus* leaf powder prepared by grinding the leaves in liquid nitrogen. The initial pH of the NaCl-containing suspension medium was acidified to pH 2.0 in one trial, basified to pH 9.0 in another trial and was unaltered (pH 6.2) in a third trial, each trial being run in duplicate. The samples were sonicated for 10 minutes and then centrifuged for 30 min. at 23,000 g. The supernatant was removed and extracted 3 times with equal volumes of ethyl acetate. This was dried down and the residue was taken up in methanol for HPLC analysis. HPLC was performed on a C-8 reverse phase 5 um column, using a solvent gradient of methanol and water with tetra-butyl ammonium phosphate as modifier.

| Results: | |
|---|---|
| Initial pH | Yield of AVLB (% of dry wt) |
| 2.0 | 0.099 |
| 6.2 | 0.066 |
| 9.0 | 0.000 |

An acidic pH therefore enhances the yield of anhydrovinblastine.

EXAMPLE 2

Narrow Spectrum Analysis of pH Effect

Duplicate samples of 1 gram fresh weight leaf powder as described in Example 1 were extracted initially with 3 ml HCl at various concentrations followed by centrifugation and organic extraction as outlined in Example 1. The results, analyzed by TLC are presented below. The pH values are given both for the pH prior to leaf powder addition and for the pH after addition of leaf powder.

| | Results: | | |
|---|---|---|---|
| HCl Conc. (M) | pH Before | After | AVLB (% dry weight) |
| 1.00 | nm | nm | 0 |
| 0.50 | 0.68 | 0.85 | 0 |
| 0.10 | 1.26 | 2.28 | 0 |
| 0.005 | 1.53 | 3.62 | 0.04 |
| 0.025 | 2.05 | 4.52 | 0.122 |
| 0.010 | 2.37 | 5.18 | 0.101 |
| 0.005 | 2.59 | 5.55 | 0.078 |
| 0.001 | 3.18 | 6.05 | 0.065 |

From these results, it is evident that an initial suspension medium pH of about 1.5 is required in order to recover anhydrovinblastine. This translates to a minimum suspension medium pH, after leaf powder addition of about 3.5. It will be further noted that a pH of from about 4 to 6 in the leaf-suspended medium provides desirable AVLB yields.

In a separate experiment, the effects of various acids on yield of AVLB were analyzed under conditions as described above. The results appear below:

| Acid | Conc (M) | pH Before | pH After | AVLB |
|---|---|---|---|---|
| HCl | 0.025 | 2.05 | 4.52 | 0.122 |
| | 0.010 | 2.37 | 5.18 | 0.101 |
| | 0.005 | 2.59 | 5.55 | 0.078 |
| | 0.001 | 3.18 | 6.05 | 0.065 |
| $H_2SO_4$ | 0.010 | 2.16 | 4.67 | 0.100 |
| | 0.001 | 2.92 | 5.82 | 0.062 |
| $CH_3COOH$ | 0.010 | 3.56 | 5.36 | 0.091 |
| | 0.001 | 4.20 | 5.95 | 0.067 |

Evidently, a variety of different acids can be used successfully to control pH in the reaction medium without adversely affecting yield.

EXAMPLE 3

Sodium Chloride

When leaves are extracted by the same method described in Example 1, using water at normal pH (c. 5.9), the levels of anhydrovinblastine extracted could be increased by having sodium chloride in the water.

Results

| Conc. of NaCl (M) | AVLB Yield (% of dry wt) |
|---|---|
| 0.00 | 0.041 |
| 0.23 | 0.049 |
| 0.91 | 0.059 |
| 1.14 | 0.050 |
| 2.28 | 0.066 |
| 4.56 | 0.021 |

Optimal yields of AVLB were obtained with 1 g NaCl in 7.5 ml water (i.e. at a concentrations of 2.28 M) when there was a 61% increase above samples extracted in the absence of sodium chloride.

When dilute acid was used to extract the AVLB, as described in Example 1, no further increase occurred when sodium chloride was added.

| NaCl Conc. (M) | AVLB Yield (% of dry wt) |
|---|---|
| 0.00 | 0.104 |
| 1.14 | 0.105 |
| 1.71 | 0.095 |
| 2.28 | 0.079 |
| 2.85 | 0.078 |

These results indicate that the lower pH may also cause some form of dissociation of the AVLB such that sodium chloride has no additional effect. The lower pH may also impart greater stability to the AVLB. The fall in AVLB yields as the NaCl concentration increases may be due to a salting out of the less soluble AVLB.

EXAMPLE 4

Sodium Borohydride Addition

Leaves were ground in liquid nitrogen and 1 g portions were mixed in 3 ml 0.025M HCl. 0.1M magnesium chloride and $3\times10^{-3}\%$ hydrogen peroxide were both added to this mixture. After centrifugation, the supernatant was removed and sodium borohydride was added such that a range of final concentrations from 0 to 3.33 mg/ml could be tested. Results of HPLC analysis for AVLB are given below:

| Sodium Borohydride Final Conc. (mg/ml) | AVLB Yield (% of dry weight) |
| --- | --- |
| 0 | .102 |
| 0.067 | .161 |
| 0.167 | .172 |
| 0.333 | .171 |
| 0.666 | .207 |
| 1.667 | .164 |
| 3.333 | .167 |

Thus, addition of sodium borohydride to the acidic extract will enhance the yields of AVLB. This must be done after the centrifugation step—if $NaBH_4$ is added prior to centrifugation, no AVLB can be extracted.

Magnesium chloride and hydrogen peroxide were subsequently found to be unnecessary for the borohydride effect.

EXAMPLE 5

Spectral Analysis

Duplicate 1 g fresh weight samples of leaf powder (prepared by grinding in liquid nitrogen) were each mixed in 3 ml of 0.03M HCl containing 0.4 g sodium chloride. These were centrifuged at 23,000 g for 30 min. and the supernatant was extracted with ethyl acetate twice. The ethyl acetate was dried down and the remaining residue was taken up in 500 ul methanol for analysis by TLC and HPLC.

HPLC: Samples were analyzed on a C-8 HPLC column as previously described. 3',4'-anhydrovinblastine was identified by its retention time, UV spectrum and 1st derivative of the spectrum, all of which correspond with those of an authentic standard. The yield of AVLB was calculated as 0.089% of the dry weight. Vindoline, catharanthine and trace amounts of leurosine were also identified by their retention times and spectra. The calculated yields of these three alkaloids are given below:

| | % Dry Weight |
| --- | --- |
| Leurosine | 0.001 |
| Vindoline | 0.148 |
| Catharanthine | 0.142 |

TLC: Normal phase thin layer chromatography was carried out, using silica gel and a mobile phase of toluene:acetone:methanol:ammonium hydroxide (28:10:2:0.5). Anhydrovinblastine, catharanthine and vindoline were all identified by their Rf values and UV spectra which corresponded with those of authentic standards. In addition, the spots eluted by TLC were sprayed with ceric ammonium sulphate spray, revealing the characteristic colour reactions for all three alkaloids.

| | Rf Values on TLC | | |
| --- | --- | --- | --- |
| | Anhydro-VLB | Catharanthine | Vindoline |
| Sample | .37 | .59 | .45 |
| Standard | .37 | .59 | .44 |

EXAMPLE 6

Sonication Effect 2.5 g samples of fresh leaf powder were extracted as described in Example 1 at acidic pH using dilute HCl (0.03M). Duplicate incubations were sonicated for various time intervals, after which they were filtered through miracloth. The filtrate was centrifuged and the resultant supernatant extracted with ethyl acetate as before.

| | Results |
| --- | --- |
| Sonication Time (in minutes) | Yield of AVLB (% of Dry Wt) |
| 0 | 0.104 |
| 15 | 0.094 |
| 30 | 0.090 |
| 60 | 0.067 |

These results show that sonication is unnecessary and that if such incubation is prolonged there is actually a decrease in the yield of AVLB possibly due to aerial oxidation. Accordingly, sonication is preferably avoided in an AVLB extraction process.

EXAMPLE 7

Enzyme Digestion of Leaf Material

Powdered leaf material samples (1 gram fresh weight) were incubated with various enzyme preparations at room temperatures for one hour. Double-distilled water was used as the extractive aqueous medium which was centrifuged and extracted with organic solvent as usual. The results appear below:

| | | | Alkaloid Conc. (% of dry wt.) | |
| --- | --- | --- | --- | --- |
| Enzyme | Conc. | AVLB | Catharanthine | Vindoline |
| Macerozyme | 0.2% | .045 | .122 | .393 |
| (a crude pectinase) | 0.4% | .073 | .163 | .382 |
| Driselase | 2.0% | .049 | .126 | .328 |
| (crude preparation of laminarinase, xylanase and cellulase) | 4.0% | .039 | .128 | .342 |
| Beta-Glucosidase | 10 units | .020 | .068 | .260 |
| | 20 units | .008 | .044 | .204 |
| Control | | .010 | .054 | .209 |

The enhanced alkaloid yield which results when Macerozyme and Driselase (both products of Yakult Honsha Co. Ltd., Japan) are used is a result most likely of the release of alkaloids from the cell wall matrix of the *C. roseus* tissue.

EXAMPLE 8

Enzyme Digestion and Acidification

Duplicate 1 g portions of leaves (ground in liquid nitrogen) were either:
1. incubated with 0.4% macerozyme in 3 ml water for 1 hour, followed by centrifugation and extraction of the supernatant as normal, or
2. 0.1M HCl was added to the mixture of leaves and water (3 ml) to give final pH of 4.5 which was centrifuged and extracted as normal, or
3. Enzyme incubation was performed as in 1, followed by acid addition as in 2.—centrifuged and extracted as normal.

| Treatment | Alkaloid content (mg) | | |
|---|---|---|---|
| | AVLB | Catharanthine | Vindoline |
| .4% macerozyme | 93.1 | 433.5 | 323.1 |
| Acid | 90.6 | 402.6 | 307.2 |
| .4% macerozyme + acid | 132.9 | 428.8 | 328.1 |

Thus, a combination of enzyme treatment followed by acidification enhanced the yield of AVLB by 43% over enzyme treatment per se.

EXAMPLE 9

Mass Spectrophotometry

A sample of AVLB extracted from leaves was purified by collection of the appropriate fraction off the HPLC. The normal HPLC gradient was run with methanol, water and 0.1% triethylamine. The fraction collected was then dried down and analyzed by electron impact mass spectrophotometry. The fragmentation pattern obtained was the same as that for an authentic sample of 3',4'-anhydrovinblastine. High resultion data showed that it had a mass of 792.4107 units (with a deviation of 0.9 milli mass units from theoretical value).

EXAMPLE 10

Identification of Vinblastine 100 g (fresh weight) of leaves were ground in 300 ml of 0.025M HCl in a Waring blender. Debris was removed by centrifugation and the supernatant was extracted with ethyl acetate. The ethyl acetate was evaporated off and the residue taken up in a small volume of methanol which was streaked on a preparative TLC plate and separated, using toluene:acetone:methanol:N-$H_4OH$ (28:10:2:0.5). A band with the same Rf value as a VLB standard was detected and scraped off the plate. This was extracted from the silica using methanol:dichloromethane (2:1) with 1.55 triethylamine. The solvent was then removed by evaporation and the remaining alkaloid was repurified on a preparative TLC plate using diethyl ether:chloroform:methanol (50:35:20). A band with the same Rf value as a VLB standard was removed and extracted as before. The solvent was evaporated off and the remaining alkaloid was dissolved in a small amount of dichloromethane, filtered and then dried again. The alkaloid was analyzed with desorption electron impact mass spectrophotometry and an ion corresponding to VLB was observed. High resolution data gave an accurate mass that was within 0.8 milli mass units of the theoretical value for vinblastine.

EXAMPLE 11

Effect of Sodium Hydroxide and Ammonium Hydroxide Addition 1 g portions of leaves (ground in liquid nitrogen) were extracted with 0.025M HCl in the normal manner. After centrifugation, the pH of the supernatant was increased to 7.3 or 9.0 with either NaOH or $NH_4OH$. In addition, leaves suspended in acid (0.025M HCl) were treated with 0.5 g NaCl and after centrifugation the pH was increased to 7.3 with either $NH_4OH$ or NaOH. Appropriate controls (i.e. without base) were also run.

| Results (from HPLC Analysis) | | |
|---|---|---|
| | pH | AVLB (% dry weight) |
| Controls | | .124 |
| + $NH_4OH$ | 7.3 | .116 |
| + NaOH | 7.3 | .090 |
| + $NH_4OH$ | 9.0 | .076 |
| + NaOH | 9.0 | .084 |
| NaCl (0.5 g) | | .089 |
| NaCl + $NH_4OH$ | 7.3 | .070 |
| NaCl + NaOH | 7.3 | .068 |

Thus, when AVLB is to be extracted it is preferred not to increase the pH of the aqueous medium prior to two phase extraction.

EXAMPLE 12

Effect of Hydrogen Peroxide Addition 1 g portions of leaf powder were mixed in with 3 ml of 0.025M HCl and a range of $H_2O_2$ concentrations were added. After centrifugation, sodium borohydride was added to supernatant at a final concentration of 0.67 mg/ml, and extraction with ethyl acetate was performed as usual.

| Results (from HPLC Analysis) | |
|---|---|
| $H_2O_2$ Conc. (mm) | AVLB (ug) |
| 0 | 372 |
| 1 | 359 |
| 2 | 360 |
| 4 | 375 |
| 8 | 445 |
| 12 | 461 |
| 20 | 444 |

Thus, the addition of $H_2O_2$ at a concentration of above 8 mM serves to enhance the yields of AVLB from leaves.

What is claimed is:

1. A process for extracting an alkaloid from the soluble component of an acidic, aqueous extract of *C. roseus* tissue which comprises treating said soluble component with a reducing agent and extracting the treated soluble component with an organic solvent.

2. The process according to claim 1 wherein the reducing agent is sodium borohydride.

3. The process according to claim 2 wherein the organic solvent is ethyl acetate.

4. A process for extracting 3',4'-anhydrovinblastine from *Catharanthus roseus* tissue which comprises the steps of (A) extracting the tissue with an aqueous medium having an acidic pH, (B) separating the soluble component of the resulting extract from the insoluble component, (C) treating the soluble component with a reducing agent and, (D) extracting the treated soluble component with organic solvent.

5. The process according to claim 4 wherein the reducing agent is sodium borohydride.

6. The process according to claim 5 wherein the concentration of the sodium borohydride in the treated solution is in the range from 0.05 to 4.0 mg/mL.

7. The process according to claim 4 wherein the pH of the soluble component is in the range from 3.5 to 6.5.

8. The process according to claim 4 wherein said aqueous medium is selected from water, acidified water and salted water.

9. The process according to claim 4 wherein said aqueous medium is acidified water.

10. The process according to claim 9 wherein said aqueous medium is water acidified with hydrochloric acid.

11. The process according to claim 4 wherein said aqueous medium is salted water.

12. The process according to claim 11 wherein said aqueous medium comprises sodium chloride, the molarity of which is in the range from 0.9M to 3.0M.

13. The process according to claim 4 wherein, after the extraction of the tissue with an aqueous medium having an acidic pH, hydrogen peroxide is added.

14. The process according to claim 13 wherein amount of hydrogen peroxide added is greater than 8 mM.

15. The process according to claim 4 wherein the *C. roseus* tissue is fresh tissue or fresh tissue which had been frozen.

16. The process according to claim 15 wherein the *C. roseus* tissue is digested with cell wall digesting enzymes prior to extraction.

17. A process for extracting 3',4'-anhydrovinblastine from *Catharanthus roseus* tissue which comprises the steps of
(A) grinding fresh *C. roseus* tissue in liquid nitrogen;
(B) digesting the ground tissue with enzyme to free alkaloids associated with structural plant tissue;
(C) extracting the tissue obtained in (B) with an aqueous acid medium;
(D) adding to the extraction solution obtained in (C), hydrogen peroxide;
(E) centrifuging to separate a soluble component and an insoluble component;
(F) treating the soluble component with sodium borohydride and;
(G) extracting the treated soluble component with ethyl acetate.

18. A 3',4'-anhydrovinblastine-containing extract whenever prepared by the process according to claim 17.

* * * * *